United States Patent [19]
Reinke et al.

[11] Patent Number: 6,091,982
[45] Date of Patent: Jul. 18, 2000

[54] DIAGNOSTIC INSTALLATION WITH A MOBILE SIGNAL PICK-UP UNIT AND A STATIONARY EVALUATION UNIT REMOTE THEREFROM

[75] Inventors: Michael Reinke, Darmstadt; Ulrich Schulze-Ganzlin, Lorsch, both of Germany

[73] Assignee: Sirona Dental Systems GmbH & Co. KG, Bensheim, Germany

[21] Appl. No.: 08/945,737

[22] PCT Filed: Apr. 23, 1996

[86] PCT No.: PCT/DE96/00700

§ 371 Date: Jan. 23, 1998

§ 102(e) Date: Jan. 23, 1998

[87] PCT Pub. No.: WO96/34556

PCT Pub. Date: Nov. 7, 1996

[30] Foreign Application Priority Data

May 4, 1995 [DE] Germany .......................... 195 16 451

[51] Int. Cl.[7] ........................................................ A61B 5/05
[52] U.S. Cl. ............................................. 600/407; 378/91
[58] Field of Search .................................. 600/483, 484, 600/407; 378/91; 359/110

[56] References Cited

U.S. PATENT DOCUMENTS

| | | |
|---|---|---|
| 4,935,635 | 6/1990 | O'Harra . |
| 5,005,126 | 4/1991 | Haskin . |
| 5,053,883 | 10/1991 | Johnson . |
| 5,434,418 | 7/1995 | Schick . |

FOREIGN PATENT DOCUMENTS

| | | |
|---|---|---|
| 0 299 490 | 1/1989 | European Pat. Off. . |
| 0 544 974 | 6/1993 | European Pat. Off. . |
| WO 91/16850 | 11/1991 | WIPO . |
| WO 95/13198 | 6/1994 | WIPO . |
| WO 96/03917 | 2/1996 | WIPO . |

*Primary Examiner*—Marvin M. Lateef
*Assistant Examiner*—Ali M. Imam
*Attorney, Agent, or Firm*—Hill & Simpson

[57] ABSTRACT

According to the invention, a mobile signal pick-up means (11) of a diagnostics installation comprises a radiation receiver (12) for generating electrical signals dependent on the radiation shadow of a transirradiated subject, an image acquisition system (15), a calculating and storage unit (21), a display (22) as well as a communication means. A stationary evaluation means (5, 6, 7, 8) comprising a communication means is provided. The communication means are implemented as bidirectional communication means and serve for the signal transmission between the mobile signal pick-up means (11) and the stationary evaluation means (5, 6, 7, 8).

15 Claims, 4 Drawing Sheets

| PC | HANDY |
|---|---|
| PATIENT SELECTION (BY DIALOG) | IDLE/OFF |
| EXPOSURE STANDBY | IDLE/OFF |
| HANDY-SELECTION (BY DIALOG) | IDLE/OFF |
| INITIALIZATION<br>.COMMUNICATION SET-UP<br>.IDENTIFICATION<br>.STATUS<br>.MEMORY CHECK | ACTIVE, DISPLAY STATUS:<br>.ERROR<br>.LOAD STATUS<br>.NAME OF INTENDED PATIENT |
| ENABLE EXPOSURE STANDBY, OR ABORT | ACTIVE |
| RADIATION | ACTIVE |
| TRANSMIT IMAGE & STORE & POST-PROCESS IN PC | ACTIVE, TRANSMIT IMAGE |
| ABORT, OR RENEWED ENABLE OF EXPOSURE STANDBY | IDLE OR ACTIVE |

FIG 4

DIAGNOSTIC INSTALLATION WITH A MOBILE SIGNAL PICK-UP UNIT AND A STATIONARY EVALUATION UNIT REMOTE THEREFROM

BACKGROUND OF THE INVENTION

1. Field of the Invention

The present invention is directed to a medical diagnostic installation of the type having a mobile signal pick-up unit in communication with at least one stationary evaluation unit, the stationary evaluation unit being disposed remote from the mobile signal pick-up unit.

2. Description of the Prior Art and Related Subject Matter

A medical diagnostic installation of the above general type is disclosed in European Application 0 544 974.

X-ray diagnostic installations are known that include a pick-up unit composed of a radiation transmitter and a radiation receiver as well as a stationary evaluation unit in communication therewith. The electrical signals acquired upon transirradiation of a subject are thereby supplied to the stationary evaluation unit via cable. The stationary evaluation unit converts these signals into image signals that can then be displayed on a monitor as an image of the subject.

PCT Application WO 96/03917, was published after the effective date for applying prior art against the subject matter of the present application, discloses a dental X-ray diagnostic installation wherein a lap top can be provided with components for wireless data transmission. The lap top can be linked to an existing computer network. An X-ray image acquisition card can be provided with suitable means for wireless transmission of the data from a sensor into the computer unit (lap top), whereby the means for the wireless transmission can be implemented as infrared transmission and reception means. An image of the examination subject can be displayed on the monitor of the computer unit (lap top).

U.S. Pat. No. 5,434,418, was not published prior to the effective date for applying prior art against the subject matter of the present application, discloses an X-ray diagnostic installation, whereby the data of an intra-oral sensor can be transmitted via a transmitter to an evaluation computer. The evaluation computer calculates an image of the examination subject from the signals of the sensor.

SUMMARY OF THE INVENTION

An object of the present invention is to provide a medical diagnostic installation of the type having a mobile signal pick-up unit which communicates with a stationary evaluation unit remote therefrom, which allows economic installation and which can be operated in a user-friendly manner.

This object is achieved in accordance with the principles of the present invention in a diagnostic installation having a mobile signal pick-up unit which includes a signal acquisition stage which generates electrical signals, and which is in communication with a stationary evaluation unit by means of a bidirectional communication linkage between the signal pick-up unit and the stationary evaluation unit, and wherein the stationary evaluation unit includes a calculating and storage stage and a display, with only status and error messages being able to be displayed on the display.

An advantage of the invention is that the electrical signals generated by the signal acquisition stage are picked up via the mobile signal pick-up unit and may be stored and supplied to the stationary evaluation unit by bidirectional communication or can be interrogated by the stationary evaluation unit. The energy consumption can be kept slight due to the display being used only for the display of status and error messages.

The mobile signal pick-up unit can be advantageously utilized in a plurality of examination rooms, so that only one mobile signal pick-up unit is required. It is thereby advantageous when the signal transmission ensues wirelessly. When a plurality of examination rooms are provided, it can also be advantageous when further stationary evaluation units and, potentially, further mobile signal pick-up units are also provided that are in communication with one another via a network. The evaluation of the signals acquired from the mobile signal pick-up units can thus be undertaken by one of the stationary evaluation units.

DESCRIPTION OF THE DRAWINGS

FIG. 4 describes an exposure sequence which takes place in the x-ray diagnostic installation of FIG. 1.

DESCRIPTION OF THE PREFERRED EMBODIMENTS

Figure 1:
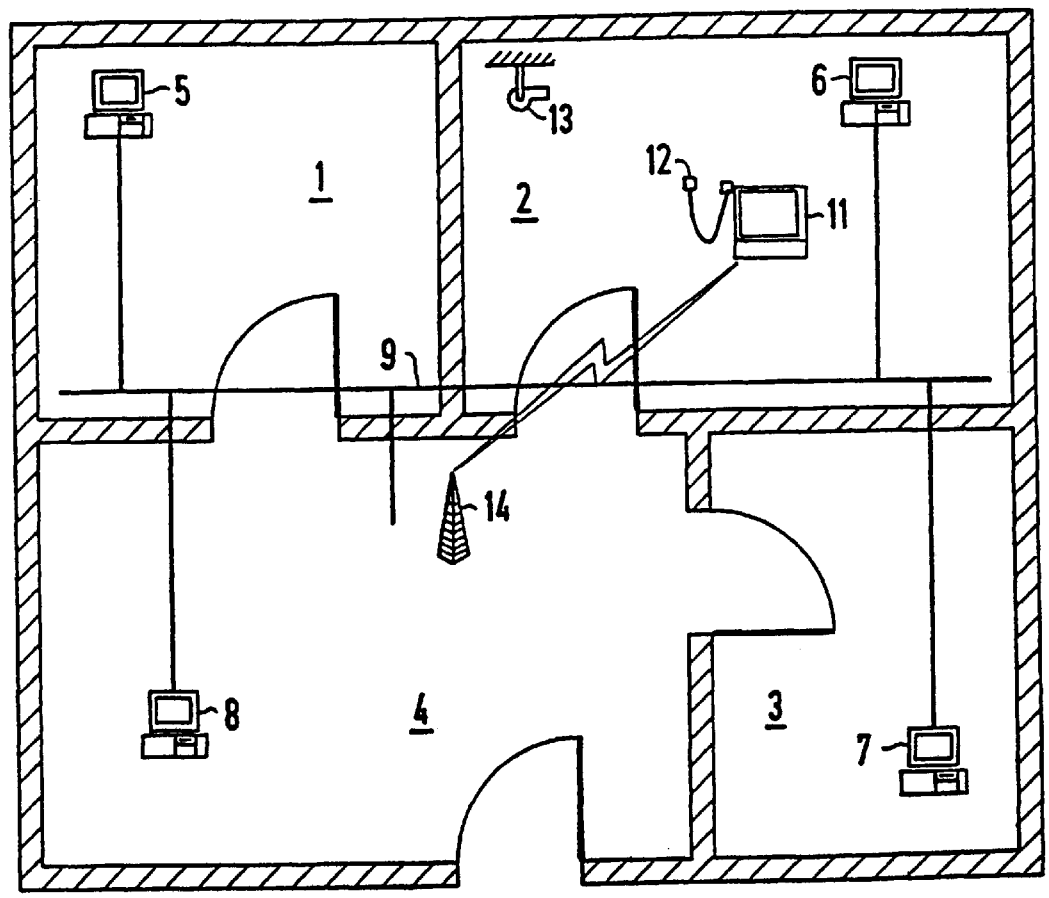
FIG. 1 is a schematic illustration of an x-ray diagnostics installation located in a number of examination rooms, constructed in accordance with the principles of the present invention.

FIG. 1 shows an exemplary embodiment of an X-ray diagnostics installation of the invention. This X-ray diagnostics installation comprises different rooms 1, 2, 3, 4 in which computers, for example personal computers 5, 6, 7, 8, are provided as stationary evaluation units, these being in communication with one another via a data network 9. A mobile signal pick-up unit 11 is present in one room 2. This mobile signal pick-up unit 11 has a radiation receiver 12 that converts the radiation shadow produced upon transirradiation of an examination subject by radiation of a radiation transmitter 13 into electrical signals. The mobile signal pick-up unit 11 is in bidirectional communication with the network 9 and, thus, with the computers 5, 6, 7, 8 via a base station 14.

Figure 2:
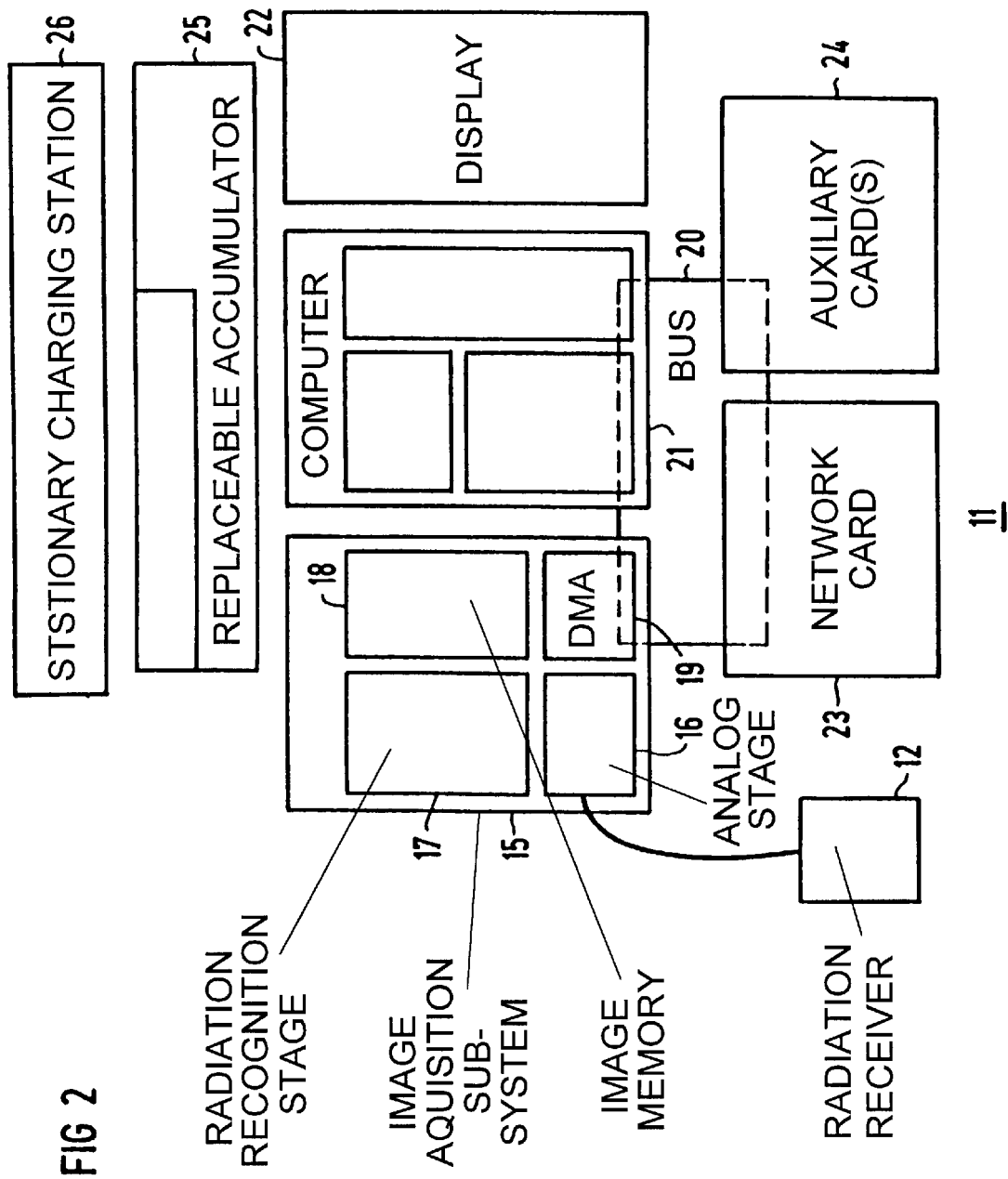
FIG. 2 is a block diagram showing the basic components of a mobile signal pick-up unit of the x-ray diagnostic installation of FIG. 1.

An exemplary embodiment of a mobile signal pick-up unit 11 shall now be explained in greater detail with reference to FIG. 2. As already explained, this mobile signal pick-up unit 11 has a radiation receiver 12 whose signals are supplied to an image acquisition sub-system 15 that comprises an analog stage 16, a radiation recognition stage 17, a local image memory 18 as well as a DMA stage 19. In the analog stage 16, the analog signals output from the radiation receiver 12 are converted into digital signals with an analog-to-digital converter. These digital signals are deposited in a memory (RAM—random memory), which can ensue especially fast when a sub-system (DMA) that has direct access to this memory is employed therefor. The image acquisition system is connected via a bus 20 to a local computer 21, a display 22, a network card 23 as well as further auxiliary cards 24.

The radiation receiver 12 is preferably operated in three phases:

1. Readiness (arbitrarily long); incident radiation is detected.
2. After radiation detection has ensued, a fastest possible switch is made into the integration phase in which the radiation receiver 12 converts the X-ray shadowgram into a two-dimensional charge image.

3. Clocking the charge image out into the image acquisition sub-system 17 with subsequent digitization and transmission to the computer 5, 6, 7, 8.

A replaceable accumulator 25 that can be supplied with energy from a stationary charging station 26 can be provided for voltage supply of the mobile signal pick-up unit 11. The charging station can thereby serve as stationary table or wall mount that enables an unproblematical and fast manipulation. So that the mobile signal pick-up unit 11 can be dimensioned small and cost-beneficially manufactured and exhibits a low power consumption, it is advantageous when no possibility for image display or for patient dialogue is provided. The user dialogue ensues via the computer or computers 5, 6, 7, 8, whereby the mobile signal pick-up unit 11 displays status and/or error messages with an alphanumerical display or via LEDs. Likewise, an image display with a flat picture screen, for example LCD, is also meaningful.

Figure 3:
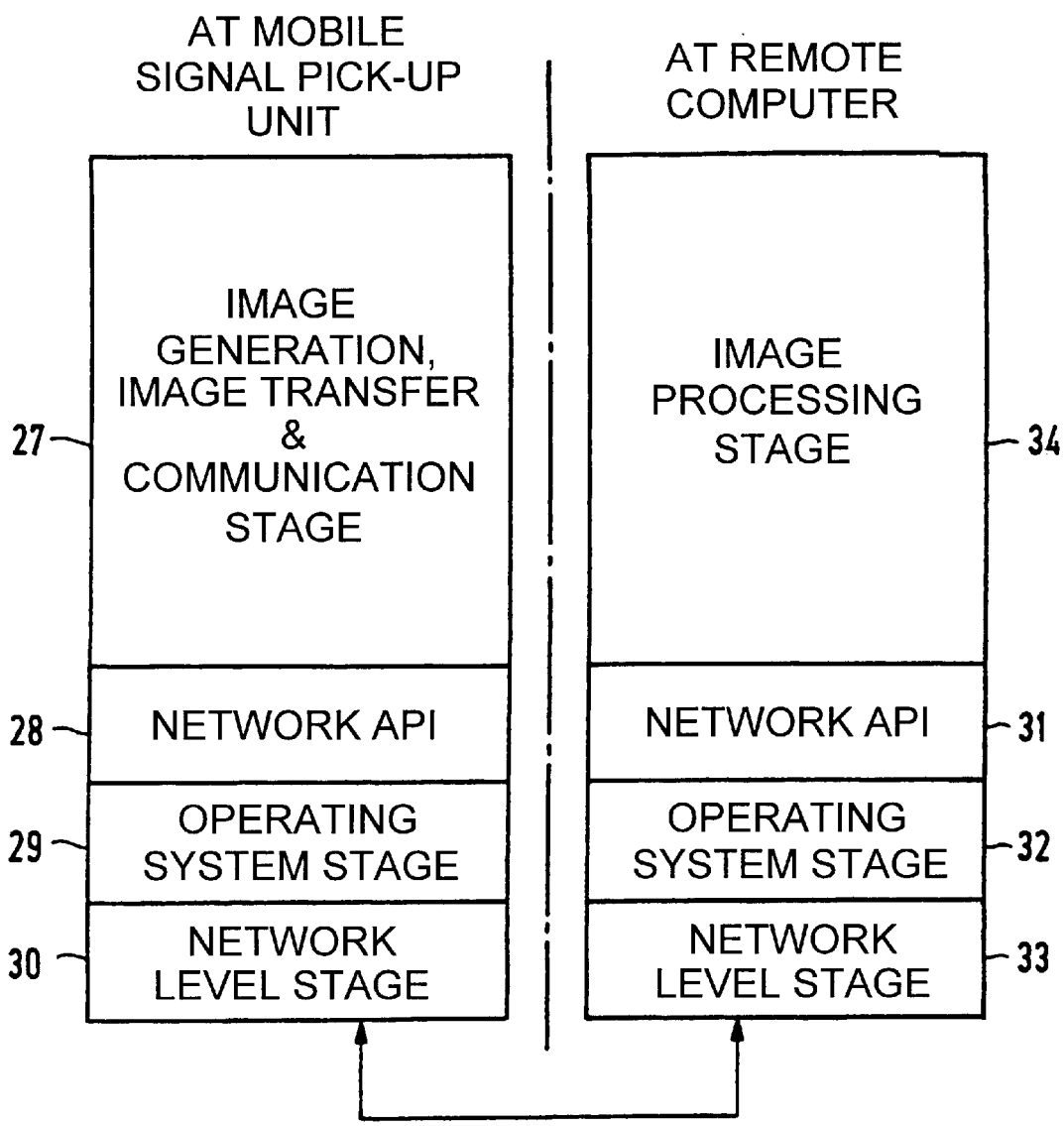
FIG. 3 illustrates a network programming interface of the x-ray diagnostic installation of FIG. 1.

FIG. 3 shows a block circuit diagram of a network programming interface between the mobile signal pick-up unit 11 and the computer 5, 6, 7, 8. The mobile signal pick-up unit 11 comprises a first block 27, wherein image generation, image transfer and communication between the mobile signal pick-up unit 11 and the computer or computers 5, 6, 7, 8 takes place. As already explained, the image generation comprises the three operating phases:

1. Readiness,
2. Radiation detection, and
3. Clocking the signals of the radiation receiver 12 out via the analog-to-digital converter and the DMA and clocking them into the RAM of the mobile signal pick-up unit 11.

The image transfer, i.e. the transmission of the signals corresponding to the received radiation shadow ensues from the RAM to the computer or computers 5, 6, 7, 8 via a network card. The communication between the mobile signal pick-up unit 11 and the computer or computers 5, 6, 7, 8 thereby ensues via a bidirectional transmission of not only image data but also for monitoring purposes, error messages and status displays. A further block 28 with respect to the network API (Application Programming Interface), a block 29 with respect to the operating system and a block 30 with respect to the network level are also provided. The block circuit diagram representing each of the computer or computers 5, 6, 7, 8 also contains blocks corresponding to the blocks 28 through 30, for example a server and, additionally, a block 34 for the image processing of the image signals of the radiation receiver 12 for the patient selection and patient allocation as well as for image archiving. A plurality of steps that are passed in what are referred to as layers are required for the data transmission between the computer or computers 5, 6, 7, 8 as well as between the computer of the mobile signal pick-up unit 11 and the computer or computers 5, 6, 7, 8. These layers are partly standardized, and appropriate software protocols exist therefor. This software must be present both on the mobile signal pick-up unit 11 as well as on the computer or computers 5, 6, 7, 8 so that the information to be transmitted (image data, status) can be exchanged between the blocks 27 and 34.

An exemplary embodiment of an executive sequence for producing an X-ray exposure in a bidirectional communication system is shown, for example, in FIG. 4 and particularly refers to the communication via a radio network (radio LAN).

A distributed client-server solution has thereby proven especially advantageous as software structure. As a result, an arbitrary plurality of mobile signal pick-up unit 11 can communicate via the network with what is likewise an arbitrary plurality of stationary evaluation means. The job of the client is the acquisition of the raw image data and the forwarding of these data to one of the computer or computers 5, 6, 7, 8. The latter has the job of further-processing these raw data and archiving them in patient-related fashion.

Within the scope of the invention, the radiation receiver 12 can be not only for the conversion of an X-ray shadowgram but can also be a means for measuring a 3-D image for tooth restoration (CEREC), an intro-oral color video camera for diagnosis, a means for measuring dental pocket depth, a means for measuring the tooth stability in the jaw (PERIOTEST), a means for measuring and checking the occlusion and/or a means for measuring chemical data (pH value) of the saliva. It will be apparent to those of ordinary skill in the art that each of the aforementioned means will include an appropriate control and acquisition system.

It should be assured in the bidirectional communication that the signals are reliably transmitted from the mobile signal pick-up unit 11 to the computer or computers 5, 6, 7, 8 and in a form that the correct reception of the image data is acknowledged and potentially repeated in case of error. This important security aspect serves for radiation hygiene.

Although modifications and changes may be suggested by those skilled in the art, it is the intention of the inventors to embody within the patent warranted hereon all changes and modifications as reasonably and properly come within the scope of their contribution to the art.

We claim:

1. A diagnostic medical installation comprising:

A mobile signal pick-up unit comprising signal acquisition means adapted for intra-oral interaction with a subject for acquiring signals containing dental information and for generating electrical signals corresponding thereto;

stationary evaluation means for evaluating said electrical signals, said stationary evaluation means being disposed remote from said mobile signal pick-up unit;

bidirectional communication means for transmitting at least said electrical signals from said signal pick-up unit to said stationary evaluation means and for transmitting from said stationary evaluation means to said mobile signal pick-up unit; and said mobile signal pick-up unit including calculating and storage means for acting on said electrical signals, and display means for displaying only messages selected from the group consisting of status messages and error messages associated with said electrical signals.

2. A diagnostic installation as claimed in claim 1 wherein said display means comprises an alphanumeric display.

3. A diagnostic installation as claimed in claim 1 wherein said display means comprises an LED display.

4. A diagnostic installation as claimed in claim 1 wherein said display means comprises a liquid crystal display.

5. A diagnostic installation as claimed in claim 1 wherein said communication means comprises a wireless communication means.

6. A diagnostic installation as claimed in claim 1 wherein said stationary evaluation means comprises a plurality of identical stationary evaluation units, each in communication via said communication means with said mobile signal pick-up unit.

7. A diagnostic installation as claimed in claim 1 further comprising a plurality of further mobile signal pick-up units, and a network connecting said mobile signal pick-up unit and each of said further mobile signal pick-up units, said network being connected to said communication means and allowing communication of each of said mobile signal pick-up unit and said further mobile signal pick-up units with said stationary evaluation means.

8. A diagnostic installation as claimed in claim 1 wherein said stationary evaluation means comprises a plurality of identical stationary evaluation units, and a network connecting each of said stationary evaluation units to each other and to said communication means for allowing any of said stationary evaluation units to communicate with said mobile signal pick-up unit.

9. A diagnostic installation as claimed in claim 1 wherein said signal acquisition means comprises a penetrating radiation receiver which generates electrical signals dependent on a radiation shadow of a transirradiated subject.

10. A diagnostic installation as claimed in claim 9 wherein said signal acquisition means comprises means for obtaining a three-dimensional image for tooth restoration.

11. A diagnostic installation as claimed in claim 9 wherein said signal acquisition means comprises an intra-oral color camera for generating said electrical signals.

12. A diagnostic installation as claimed in claim 9 wherein said signal acquisition means comprises means for measuring a tooth pocket depth.

13. A diagnostic installation as claimed in claim 9 wherein said signal acquisition means comprises means for measuring stability of a tooth in a jaw.

14. A diagnostic installation as claimed in claim 9 wherein said signal acquisition means comprises means for measuring and checking a dental occlusion.

15. A diagnostic installation as claimed in claim 1 wherein said signal acquisition means comprises means for measuring chemical data of saliva.

* * * * *